(12) United States Patent
Damha et al.

(10) Patent No.: US 7,501,503 B2
(45) Date of Patent: Mar. 10, 2009

(54) COMPOSITIONS AND METHODS FOR INHIBITING RNASE H ACTIVITY OF RETROID REVERSE TRANSCRIPTASE

(75) Inventors: Masad J. Damha, St. Hubert (CA); Rami N. Hannoush, Cambridge, MA (US); Kyung-Lyum Min, Montreal (CA); Sandra Carriero, St. Lazare (CA)

(73) Assignee: McGill University, Montreal QC (CA)

( * ) Notice: Subject to any disclaimer, the term of this patent is extended or adjusted under 35 U.S.C. 154(b) by 0 days.

(21) Appl. No.: 10/748,475

(22) Filed: Dec. 30, 2003

(65) Prior Publication Data

US 2004/0138166 A1 Jul. 15, 2004

Related U.S. Application Data

(60) Provisional application No. 60/509,716, filed on Oct. 7, 2003, provisional application No. 60/437,568, filed on Dec. 31, 2002.

(51) Int. Cl.
*C07H 21/04* (2006.01)
(52) U.S. Cl. .................... 536/24.5; 536/23.1; 536/24.33
(58) Field of Classification Search ................ 536/23.1, 536/24.5, 24.3, 24.31, 24.33
See application file for complete search history.

(56) References Cited

OTHER PUBLICATIONS

Ray et al. Peptide nucleic acid (PNA); its medical and biotechnical applications and promose for the future. FASEB J. 2000 (9): 1041-1060.*
Denisov et al. Solution structure of an arabinonucleic acid (ANA)/RNA duplex in a chimeric hairpin: comparison with 2'-fluoro-ANA/RNA and DNA/RNA hybrids. Nucleic Acid Research, Nov. 2001, vol. 29, No. 21. Oxford University Press.*
Joshi et al. Potent Inhibitors of Human Immunodeficiency Virus Type 1 Replication by Template Analog Reverse Transcriptase Inhibitors Derived by SELEX (Systematic Evolution of Ligands by Exponential Enrichment). Journal of Virology, Jul. 2002, p. 6545-6557.*
Andreola et al., "DNA Aptamers Selected against the HIV-1 Rnase H Display in Vitro Antiviral Activity", Biochemistry 2001 40:10087-10094.
Borkow et al., "Inhibition of the Ribonuclease H and DNA Polymerase Activities of HIV-1 Reverse Transcriptase by N-(4-tert-Butylbenzoyl)2-hydroxy-1-naphthaldehyde Hydrazone", Biochemistry 1997 36:3179-3185.
Chen et al., "Selection of High-Affinity RNA Ligands to Reverse Transcriptase: Inhibition of cDNA Synthesis and RNASE H Activity", Biochemistry 1994 33:8746-8756.
Clusel et al., "Ex vivo regulation of specific gene expression by nanomolar concentration of double-stranded dumbbell oligonucleotides", Nucleic Acids Research 1993 21(15):3405-3411.
Hannoush et al., "Remarkable Stability of Hairpins Containing 2',5'-Linked RNA Loops", J. Am. Chem. Soc. 2001 123:12368-12374.
Lim et al., "Sequence-independent inhibition of RNA transcription by DNA dumbbells and other decoys", Nucleic Acids Research 1997 25(3):575-581.
Loya et al., "Illimaquinone, a Selective Inhibitor of the RNase H Activity of Human Immunodeficiency Virus Type 1 Reverse Transcriptase", Antimicrobial Agents and Chemotherapy 1990 34(10):2009-2012.
Loya et al., "The Interaction of Illimaquinone, a Selective Inhibitor of the RNase H Activity, with the Reverse Transcriptases of Human Immunodeficiency and Murine Leukemia Retroviruses", J. Biol. Chem. 1993 268(13):9323-9328.
Mizrahi et al., "Mutagenesis of the Conversed Aspartic Acid 443, Glutamic Acid 478, Asparagine 494, and Aspartic Acid 498 Residues in the Ribonuclease H Domain of p66/p51 Human Immunodeficiency Virus Type I Reverse Transcriptase", J. Biol. Chem. 1994 269(30):19245-19249.
Park et al., "Inhibition of HIV-1 Replication by a New Type of Circular Dumbbell RNA/DNA Chimeric Oligonucleotides", Biochemical and Biophysical Research Communications 2000 270:953-960.
Tan et al., "Inhibition of the RNASE H Activity of HIV Reverse Transcriptase by Azidothymidylate", Biochemistry 1991 30(20):4831-4835.
Tarrago-Litvak et al., "Inhibitors of HIV-1 Reverse Transcriptase and Integrase:Classical and Emerging Therapeutical Approaches", Current Pharmaceutical Design 2002 8:595-614.
Wasner et al., "Physicochemical and Biochemical Properties of 2',5'-Linked RNA and 2',5':3',5'-RNA "Hybrid" Duplexes", Biochemistry 1998 37:7478-7486.
Gao et al., "Phosphorothioate Oligonucleotides Are Inhibitors of Human DNA Polymerases and RNase H:Implications for Antisense Technology" Molecular Pharmacology 1992 41:223-229.
Zhan et al., "Catalytically Distinct conformations of the Ribonuclease H of HIV-1 Reverse Transcriptase by Substrate Cleavage Patterns and Inhibition by Azidothymidylate and N-Ethylmaleimide", Biochemistry 1994 33:1366-1372.

* cited by examiner

*Primary Examiner*—Kimberly Chong
(74) *Attorney, Agent, or Firm*—Licata & Tyrrell P.C.

(57) ABSTRACT

The invention relates to oligonucleotide agents that inhibit RNase H activity of a retroid virus reverse transcriptase and are useful for inhibiting retroid virus proliferation and preventing or treating a retroid virus infection.

1 Claim, No Drawings

SEQUENCE LISTING

```
<160> NUMBER OF SEQ ID NOS: 58

<210> SEQ ID NO 1
<211> LENGTH: 4
<212> TYPE: RNA
<213> ORGANISM: Artificial Sequence
<220> FEATURE:
<223> OTHER INFORMATION: Synthetic loop moiety
<220> FEATURE:
<221> NAME/KEY: misc_feature
<222> LOCATION: (3)..(3)
<223> OTHER INFORMATION: "Y" represents "C" or "U"

<400> SEQUENCE: 1 uuyg                                                                      4

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(1)
<223> OTHER INFORMATION: DNA residue
<220> FEATURE:
<221> NAME/KEY: misc_feature
<222> LOCATION: (2)..(27)
<223> OTHER INFORMATION: RNA residue
<220> FEATURE:
<221> NAME/KEY: misc_feature
<222> LOCATION: (28)..(28)
<223> OTHER INFORMATION: DNA residue

<400> SEQUENCE: 2
tggacuucgg uccaaaaacu ucgguuut                                           28

<210> SEQ ID NO 3
<211> LENGTH: 5
<212> TYPE: DNA
<213> ORGANISM: Artificial Sequence
<220> FEATURE:
<223> OTHER INFORMATION: Synthetic stem moiety
<220> FEATURE:
<221> NAME/KEY: misc_feature
<222> LOCATION: (1)..(1)
<223> OTHER INFORMATION: DNA residue
<220> FEATURE:
<221> NAME/KEY: misc_feature
<222> LOCATION: (2)..(5)
<223> OTHER INFORMATION: RNA residue

<400> SEQUENCE: 3 tggac                                                                    5

<210> SEQ ID NO 4
<211> LENGTH: 5
<212> TYPE: RNA
<213> ORGANISM: Artificial Sequence
<220> FEATURE:
<223> OTHER INFORMATION: Synthetic stem moiety

<400> SEQUENCE: 4 aaaac                                                                    5

<210> SEQ ID NO 5
<211> LENGTH: 5
<212> TYPE: RNA
<213> ORGANISM: Artificial Sequence
<220> FEATURE:
<223> OTHER INFORMATION: Synthetic stem moiety

<400> SEQUENCE: 5 gucca                                                                    5

<210> SEQ ID NO 6
<211> LENGTH: 5
<212> TYPE: DNA
<213> ORGANISM: Artificial Sequence
<220> FEATURE:
<223> OTHER INFORMATION: Synthetic stem moiety
<220> FEATURE:
<221> NAME/KEY: misc_feature
<222> LOCATION: (1)..(4)
<223> OTHER INFORMATION: RNA residue
<220> FEATURE:
<221> NAME/KEY: misc_feature
<222> LOCATION: (5)..(5)
<223> OTHER INFORMATION: DNA residue
```

```
<400> SEQUENCE: 6 guuut                                                                      5

<210> SEQ ID NO 7
<211> LENGTH: 4
<212> TYPE: RNA
<213> ORGANISM: Artificial Sequence
<220> FEATURE:
<223> OTHER INFORMATION: Synthetic loop moiety

<400> SEQUENCE: 7 uucg                                                                       4

<210> SEQ ID NO 8
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: DNA residue
<220> FEATURE:
<221> NAME/KEY: misc_feature
<222> LOCATION: (2)..(14)
<223> OTHER INFORMATION: RNA residue

<400> SEQUENCE: 8
tggacuucgg ucca                                                           14

<210> SEQ ID NO 9
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 9
ggacuucggu ccaaacuucg guuu                                                24

<210> SEQ ID NO 10
<211> LENGTH: 4
<212> TYPE: DNA
<213> ORGANISM: Artificial Sequence
<220> FEATURE:
<223> OTHER INFORMATION: Synthetic stem moiety

<400> SEQUENCE: 10 gucc                                                                       4

<210> SEQ ID NO 11
<211> LENGTH: 4
<212> TYPE: DNA
<213> ORGANISM: Artificial Sequence
<220> FEATURE:
<223> OTHER INFORMATION: Synthetic stem moiety

<400> SEQUENCE: 11 ggac                                                                       4

<210> SEQ ID NO 12
<211> LENGTH: 12
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(12)
<223> OTHER INFORMATION: DNA residues
<220> FEATURE:
<221> NAME/KEY: misc_feature
<222> LOCATION: (5)..(6)
<223> OTHER INFORMATION: "u" represents deoxyuridine residues

<400> SEQUENCE: 12
ggacuucggt cc                                                         12

<210> SEQ ID NO 13
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 13
ggacttttgt cc                                                         12

<210> SEQ ID NO 14
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residue
<220> FEATURE:
<221> NAME/KEY: misc_feature
<222> LOCATION: (5)..(8)
<223> OTHER INFORMATION: RNA residue
<220> FEATURE:
<221> NAME/KEY: misc_feature
<222> LOCATION: (9)..(12)
<223> OTHER INFORMATION: DNA residue

<400> SEQUENCE: 14
ggacuucggt cc                                                         12

<210> SEQ ID NO 15
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: 2',5'-RNA residues
<220> FEATURE:
<221> NAME/KEY: misc_feature
<222> LOCATION: (9)..(12)
<223> OTHER INFORMATION: DNA residues

<400> SEQUENCE: 15
ggacuucggt cc                                                         12

<210> SEQ ID NO 16
<211> LENGTH: 12
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: 2',5'-RNA residues
<220> FEATURE:
<221> NAME/KEY: misc_feature
<222> LOCATION: (9)..(12)
<223> OTHER INFORMATION: DNA residues

<400> SEQUENCE: 16
ggacuacggt cc                                                              12

<210> SEQ ID NO 17
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: 2',5'-RNA residues
<220> FEATURE:
<221> NAME/KEY: misc_feature
<222> LOCATION: (9)..(12)
<223> OTHER INFORMATION: DNA residues

<400> SEQUENCE: 17
ggacuuuggt cc                                                              12

<210> SEQ ID NO 18
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: 2',5'-RNA residues
<220> FEATURE:
<221> NAME/KEY: misc_feature
<222> LOCATION: (9)..(12)
<223> OTHER INFORMATION: DNA residues

<400> SEQUENCE: 18
ggacuuuugt cc                                                              12

<210> SEQ ID NO 19
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: RNA residues
```

```
<220> FEATURE:
<221> NAME/KEY: misc_feature
<222> LOCATION: (5)..(8)
<223> OTHER INFORMATION: DNA residues
<220> FEATURE:
<221> NAME/KEY: misc_feature
<222> LOCATION: (9)..(12)
<223> OTHER INFORMATION: RNA residues

<400> SEQUENCE: 19
ggacuucggu cc                                                          12

<210> SEQ ID NO 20
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 20
ggacuucggu cc                                                          12

<210> SEQ ID NO 21
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(8)
<223> OTHER INFORMATION: 2',5'-RNA residues

<400> SEQUENCE: 21
ggacuucggu cc                                                          12

<210> SEQ ID NO 22
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: RNA residue
<220> FEATURE:
<221> NAME/KEY: misc_feature
<222> LOCATION: (4)..(4)
<223> OTHER INFORMATION: sugar/phosphodiester DNA composition
<220> FEATURE:
<221> NAME/KEY: misc_feature
<222> LOCATION: (5)..(8)
<223> OTHER INFORMATION: RNA residues
<220> FEATURE:
<221> NAME/KEY: misc_feature
<222> LOCATION: (9)..(9)
<223> OTHER INFORMATION: sugar/phosphodiester DNA composition
<220> FEATURE:
<221> NAME/KEY: misc_feature
<222> LOCATION: (10)..(12)
<223> OTHER INFORMATION: RNA residues

<400> SEQUENCE: 22
ggacuucggu cc                                                          12

<210> SEQ ID NO 23
<211> LENGTH: 12
<212> TYPE: DNA
<213> ORGANISM: Artificial Sequence
```

```
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: RNA residues
<220> FEATURE:
<221> NAME/KEY: misc_feature
<222> LOCATION: (4)..(4)
<223> OTHER INFORMATION: sugar/phosphodiester DNA composition
<220> FEATURE:
<221> NAME/KEY: misc_feature
<222> LOCATION: (5)..(8)
<223> OTHER INFORMATION: 2',5'-RNA residue
<220> FEATURE:
<221> NAME/KEY: misc_feature
<222> LOCATION: (9)..(9)
<223> OTHER INFORMATION: sugar/phosphodiester DNA composition
<220> FEATURE:
<221> NAME/KEY: misc_feature
<222> LOCATION: (10)..(12)
<223> OTHER INFORMATION: RNA residues

<400> SEQUENCE: 23
ggacuucggu cc                                                              12

<210> SEQ ID NO 24
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: RNA residues
<220> FEATURE:
<221> NAME/KEY: misc_feature
<222> LOCATION: (4)..(4)
<223> OTHER INFORMATION: sugar/phosphodiester DNA composition
<220> FEATURE:
<221> NAME/KEY: misc_feature
<222> LOCATION: (5)..(12)
<223> OTHER INFORMATION: RNA residues

<400> SEQUENCE: 24
ggacuucggu cc                                                              12

<210> SEQ ID NO 25
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: RNA residues
<220> FEATURE:
<221> NAME/KEY: misc_feature
<222> LOCATION: (9)..(9)
<223> OTHER INFORMATION: sugar/phosphodiester DNA composition
<220> FEATURE:
<221> NAME/KEY: misc_feature
<222> LOCATION: (10)..(12)
<223> OTHER INFORMATION: RNA residues

<400> SEQUENCE: 25
ggacuucggu cc                                                              12
```

```
<210> SEQ ID NO 26
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 2',5'-RNA residue; sugar/phosphodiester
                         composition

<400> SEQUENCE: 26
ggacuucggu cc                                                           12

<210> SEQ ID NO 27
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 2',5'-RNA residue; sugar/phosphodiester
                         composition

<400> SEQUENCE: 27
ggacuucggu cc                                                           12

<210> SEQ ID NO 28
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 2',5'-RNA residue; sugar/phosphodiester
                         composition

<400> SEQUENCE: 28
ggacuucggu cc                                                           12

<210> SEQ ID NO 29
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: sugar/phosphodiester composition
<220> FEATURE:
<221> NAME/KEY: misc_feature
<222> LOCATION: (4)..(8)
<223> OTHER INFORMATION: 2',5'-RNA residues

<400> SEQUENCE: 29
ggacuucggu cc                                                           12

<210> SEQ ID NO 30
<211> LENGTH: 12
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(3)
<223> OTHER INFORMATION: DNA residues
<220> FEATURE:
<221> NAME/KEY: misc_feature
<222> LOCATION: (4)..(4)
<223> OTHER INFORMATION: sugar/phosphodiester RNA composition
<220> FEATURE:
<221> NAME/KEY: misc_feature
<222> LOCATION: (4)..(9)
<223> OTHER INFORMATION: RNA residues
<220> FEATURE:
<221> NAME/KEY: misc_feature
<222> LOCATION: (9)..(9)
<223> OTHER INFORMATION: sugar/phosphodiester RNA composition
<220> FEATURE:
<221> NAME/KEY: misc_feature
<222> LOCATION: (10)..(12)
<223> OTHER INFORMATION: DNA residues

<400> SEQUENCE: 30
ggacuucggt cc                                                              12

<210> SEQ ID NO 31
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: DNA residues
<220> FEATURE:
<221> NAME/KEY: misc_feature
<222> LOCATION: (4)..(4)
<223> OTHER INFORMATION: sugar/phosphodiester composition
<220> FEATURE:
<221> NAME/KEY: misc_feature
<222> LOCATION: (4)..(9)
<223> OTHER INFORMATION: RNA residues
<220> FEATURE:
<221> NAME/KEY: misc_feature
<222> LOCATION: (9)..(9)
<223> OTHER INFORMATION: sugar/phosphodiester RNA composition
<220> FEATURE:
<221> NAME/KEY: misc_feature
<222> LOCATION: (10)..(12)
<223> OTHER INFORMATION: DNA residues

<400> SEQUENCE: 31
ggacuuuugt cc                                                              12

<210> SEQ ID NO 32
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: DNA residues
<220> FEATURE:
<221> NAME/KEY: misc_feature
<222> LOCATION: (4)..(4)
<223> OTHER INFORMATION: sugar/phosphodiester RNA composition
<220> FEATURE:
<221> NAME/KEY: misc_feature
<222> LOCATION: (5)..(8)
<223> OTHER INFORMATION: 2',5'-RNA residue
```

```
<220> FEATURE:
<221> NAME/KEY: misc_feature
<222> LOCATION: (9)..(9)
<223> OTHER INFORMATION: sugar/phosphodiester RNA composition
<220> FEATURE:
<221> NAME/KEY: misc_feature
<222> LOCATION: (10)..(12)
<223> OTHER INFORMATION: DNA residues

<400> SEQUENCE: 32
ggacuucggt cc                                                            12

<210> SEQ ID NO 33
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: DNA residues
<220> FEATURE:
<221> NAME/KEY: misc_feature
<222> LOCATION: (4)..(4)
<223> OTHER INFORMATION: sugar/phosphodiester RNA composition
<220> FEATURE:
<221> NAME/KEY: misc_feature
<222> LOCATION: (4)..(8)
<223> OTHER INFORMATION: 2',5'-RNA residues
<220> FEATURE:
<221> NAME/KEY: misc_feature
<222> LOCATION: (9)..(9)
<223> OTHER INFORMATION: sugar/phosphodiester RNA composition
<220> FEATURE:
<221> NAME/KEY: misc_feature
<222> LOCATION: (10)..(12)
<223> OTHER INFORMATION: DNA residues

<400> SEQUENCE: 33
ggacuucggt cc                                                            12

<210> SEQ ID NO 34
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: DNA residues
<220> FEATURE:
<221> NAME/KEY: misc_feature
<222> LOCATION: (9)..(12)
<223> OTHER INFORMATION: RNA residues

<400> SEQUENCE: 34
ggacuucggu cc                                                            12

<210> SEQ ID NO 35
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
```

```
<220> FEATURE:
<221> NAME/KEY: misc_feature
<222> LOCATION: (5)..(12)
<223> OTHER INFORMATION: RNA residues

<400> SEQUENCE: 35
ggacuucggu cc                                                              12

<210> SEQ ID NO 36
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: 2',5'-RNA residues
<220> FEATURE:
<221> NAME/KEY: misc_feature
<222> LOCATION: (9)..(12)
<223> OTHER INFORMATION: RNA residues

<400> SEQUENCE: 36
ggacuucggu cc                                                              12

<210> SEQ ID NO 37
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: 2',5'-RNA residues
<220> FEATURE:
<221> NAME/KEY: misc_feature
<222> LOCATION: (5)..(12)
<223> OTHER INFORMATION: DNA residues

<400> SEQUENCE: 37
ggacuucggt cc                                                              12

<210> SEQ ID NO 38
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: 2',5'-RNA residues
<220> FEATURE:
<221> NAME/KEY: misc_feature
<222> LOCATION: (5)..(8)
<223> OTHER INFORMATION: RNA residues
<220> FEATURE:
<221> NAME/KEY: misc_feature
<222> LOCATION: (9)..(12)
<223> OTHER INFORMATION: DNA residues

<400> SEQUENCE: 38
ggacuucggt cc                                                              12
```

```
<210> SEQ ID NO 39
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: 2',5'-RNA residues
<220> FEATURE:
<221> NAME/KEY: misc_feature
<222> LOCATION: (9)..(12)
<223> OTHER INFORMATION: DNA residues

<400> SEQUENCE: 39
ggacuucggt cc                                                           12

<210> SEQ ID NO 40
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: RNA residues
<220> FEATURE:
<221> NAME/KEY: misc_feature
<222> LOCATION: (9)..(11)
<223> OTHER INFORMATION: 2',5'-RNA residues
<220> FEATURE:
<221> NAME/KEY: misc_feature
<222> LOCATION: (12)..(12)
<223> OTHER INFORMATION: RNA residue

<400> SEQUENCE: 40
ggacuucggu cc                                                           12

<210> SEQ ID NO 41
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(11)
<223> OTHER INFORMATION: 2',5'-RNA residues
<220> FEATURE:
<221> NAME/KEY: misc_feature
<222> LOCATION: (12)..(12)
<223> OTHER INFORMATION: RNA residue

<400> SEQUENCE: 41
ggacuucggu cc                                                           12

<210> SEQ ID NO 42
<211> LENGTH: 12
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (1)..(4)
<223> OTHER INFORMATION: 2',5'-RNA residues
<220> FEATURE:
<221> NAME/KEY: misc_feature
<222> LOCATION: (5)..(8)
<223> OTHER INFORMATION: DNA residues
<220> FEATURE:
<221> NAME/KEY: misc_feature
<222> LOCATION: (9)..(12)
<223> OTHER INFORMATION: RNA residues

<400> SEQUENCE: 42
ggacuucggu cc                                                              12

<210> SEQ ID NO 43
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: 2',5'-RNA residues

<400> SEQUENCE: 43
ggacuucggu cc                                                              12

<210> SEQ ID NO 44
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: 2',5'-RNA residues

<400> SEQUENCE: 44
ggacuucggu cc                                                              12

<210> SEQ ID NO 45
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(11)
<223> OTHER INFORMATION: 2',5'-RNA residues

<400> SEQUENCE: 45
ggacuucggu cc                                                              12

<210> SEQ ID NO 46
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(11)
<223> OTHER INFORMATION: 2',5'-RNA residues
```

-continued

```
<400> SEQUENCE: 46
ggacuucggu cc                                                         12

<210> SEQ ID NO 47
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: 2',5'-RNA residues
<220> FEATURE:
<221> NAME/KEY: misc_feature
<222> LOCATION: (9)..(11)
<223> OTHER INFORMATION: 2',5'-RNA residues

<400> SEQUENCE: 47
ggacuucggu cc                                                         12

<210> SEQ ID NO 48
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(11)
<223> OTHER INFORMATION: 2',5'-RNA residues

<400> SEQUENCE: 48
ggacuucggu cc                                                         12

<210> SEQ ID NO 49
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: DNA residues
<220> FEATURE:
<221> NAME/KEY: misc_feature
<222> LOCATION: (5)..(8)
<223> OTHER INFORMATION: RNA residues
<220> FEATURE:
<221> NAME/KEY: misc_feature
<222> LOCATION: (9)..(12)
<223> OTHER INFORMATION: DNA residues

<400> SEQUENCE: 49
ttttuucgtt tt                                                         12

<210> SEQ ID NO 50
<211> LENGTH: 16
<212> TYPE: RNA
<213> ORGANISM: Artificial Sequence
<220> FEATURE:
<223> OTHER INFORMATION: Synthetic oligonucleotide

<400> SEQUENCE: 50
guggacuucg guccac                                                     16
```

```
<210> SEQ ID NO 51
<211> LENGTH: 16
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(10)
<223> OTHER INFORMATION: 2',5'-RNA residues

<400> SEQUENCE: 51
guggacuucg guccac                                                      16

<210> SEQ ID NO 52
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 52
aaacuucggu uu                                                          12

<210> SEQ ID NO 53
<211> LENGTH: 4
<212> TYPE: RNA
<213> ORGANISM: Artificial Sequence
<220> FEATURE:
<223> OTHER INFORMATION: Synthetic loop moiety

<400> SEQUENCE: 53 uacg                                                                    4

<210> SEQ ID NO 54
<211> LENGTH: 18
<212> TYPE: RNA
<213> ORGANISM: Artificial Sequence
<220> FEATURE:
<223> OTHER INFORMATION: Synthetic oligonucleotide

<400> SEQUENCE: 54
gaucugagcc ugggagcu                                                    18

<210> SEQ ID NO 55
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 55
agctcccagg ctcagatc                                                    18

<210> SEQ ID NO 56
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 56
aucucuagca gaggcgcccg aacagggaca                                       30
```

-continued

```
<210> SEQ ID NO 57
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 57
tgtccctgtt cgggcgcc                                                 18

<210> SEQ ID NO 58
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 58
atctctagca gaggcgcccg aacagggaca                                    30
```

COMPOSITIONS AND METHODS FOR INHIBITING RNASE H ACTIVITY OF RETROID REVERSE TRANSCRIPTASE

INTRODUCTION

This application claims the benefit of priority from U.S. patent application Ser. Nos. 60/437,568 filed Dec. 31, 2002 and 60/509,716 filed Oct. 7, 2003, which are incorporated herein by reference in their entireties.

BACKGROUND OF THE INVENTION

Acquired immunodeficiency syndrome (AIDS) is one of the most lethal diseases for which no complete cure has been identified. Basic research has attributed the cause of AIDS to a single-stranded RNA virus (retrovirus) referred to as human immunodeficiency virus (HIV) (Coffin, et al. (1986) *Science* 232:697; Gallo and Montagnier (1988) *Sci. Am.* 259:40). Two genetically distinct subtypes, HIV-1 and HIV-2 (Clavel, et al. (1986) *Nature* 324:691; Guyader, et al. (1987) *Nature* 326: 662), have been recognized, with the former being identified as the main causative agent of the disease.

Reverse transcriptase is an essential enzyme necessary for HIV genomic replication (DeClerq (1986) *J. Med. Chem.* 29:1561-1569; Krug and Berger (1991) *Biochemistry* 30:10614-10623; Kedar, et al. (1990) *Biochemistry* 29:3603-3611). HIV reverse transcriptase is a multi-functional enzyme having RNA- and DNA-dependent DNA polymerase activity as well as a ribonuclease H (RNase H) activity. These activities enable the enzyme to reverse transcribe viral RNA to double-stranded DNA, hence fundamentally making it one of the most challenging central drug targets in anti-retroviral therapy (Gilboa, et al. (1979) *Cell* 18:93-100). In general, reverse transcriptase inhibitors fall into one of three classes: nucleoside inhibitors (NRTIs) which inhibit viral replication by acting as chain terminators of DNA synthesis; non-nucleoside inhibitors (NNRTIs), a structurally diverse class of compounds; and oligonucleotide constructs (ONRTI); however, most reverse transcriptase inhibitors primarily target the DNA polymerase activity and not the RNase H activity of this enzyme.

RNase H activity of HIV-1 reverse transcriptase is vital for viral replication since it is specifically required to cleave the RNA portion of a DNA/RNA heteroduplex intermediate, thereby permitting the viral DNA to disengage and invade the host cell's genetic material. Furthermore, point mutations in the RNase H domain of reverse transcriptase provoke a marked decrease in the level of virus proliferation, demonstrating that a functional RNase H activity is essential for retroviral replication (Mizrahi, et al. (1994) *J. Biol. Chem.* 269:19245-19249). HIV-1 RNase H inhibition has been demonstrated in vitro, however, it is unclear whether the inhibitory agents directly bind to the RNase H domain to achieve their effect (Tarrago-Litvak, et al. (2002) *Current Pharmaceutical Design* 8:595-614).

Blocking reverse transcriptase-associated RNase H activity has mostly been demonstrated in cell-free systems. For example, the RNase H activity of reverse transcriptase may be inhibited by 3'-azidothymidylate 5'-monophosphate (AZT-MP), a major intracellular metabolite of the NNRT inhibitor AZT, with an $IC_{50}$ in the 50 µM range (Tan, et al. (1991) *Biochemistry* 30:4831-4835; Zhan, et al. (1994) *Biochemistry* 33:1366-1372). Apart from a high inhibitory concentration, the activity of AZT-MP is also dependent on the presence of a metal cation, with $Mg^{2+}$ being the most effective co-activator.

The metal chelator N-(4-tert-butylbenzoyl)-2-hydroxy-1-naphthaldehyde hydrazone (BBNH) has demonstrated potent RNase H inhibitory activity ($IC_{50}$=3.5 µM), and is effective against mutant reverse transcriptase enzymes that have a high-level of resistance to other NNRTIs (Borkow, et al. (1997) *Biochemistry* 36:3179-3185). However, BBNH also inhibits the DNA polymerase activity of reverse transcriptase, and thus may interact with more than one domain on reverse transcriptase.

Illimaquinone, a natural product of marine origin, preferentially inhibits the RNase H activity of HIV-1 reverse transcriptase, however, it is not specific to HIV-1 as it also hinders the RNase H function of HIV-2 reverse transcriptase, MLV reverse transcriptase and *E. coli* (Loya and Hizi (1993) *J. Biol. Chem.* 268:9323-9328; Loya, et al. (1990) *Antimicrob. Agents Chemother.* 34(10):2009-12).

Few ONRTIs are specific for RNase H activity of HIV-1 reverse transcriptase. ONRTIs may act by blocking the catalytic site of the enzyme or impeding the binding of the viral DNA/RNA heteroduplex to the RNase H domain. Phosphorothioate oligonucleotides have demonstrated RNase H inhibition, however they also affect the DNA polymerase activity (Gao, et al. (1992) *Mol. Pharmacol.* 41:223-229). A series of DNA aptamers with high affinity and specificity for the RNase H activity of HIV-1 reverse transcriptase have also been isolated by SELEX. The most potent inhibitors were based on a G-quartet motif with $IC_{50}$ values in the 500 nM range, however, these agents also inhibited the DNA polymerase activity of reverse transcriptase (Andreola, et al. (2001) *Biochemistry* 40:10087-10094). RNA aptamers also display non-selective dual inhibitory capacity (Chen and Gold (1994) *Biochemistry* 33:8746-8756). Duplexes consisting of 2',5'-RNA/RNA have also been shown to competitively suppress binding of the viral DNA/RNA substrate to HIV-1 reverse transcriptase without evoking its RNase H activity (Wasner, et al. (1998) *Biochemistry* 37:7478-7486); however, the effect on the polymerase activity was not indicated.

Chimeric RNA/DNA oligonucleotides bearing a sense RNA and antisense DNA strand linked by two alkyl loop structures have been investigated for their ability to inhibit HIV replication (Park, et al. (2000) *Biochem. Biophys. Res. Commun.* 270(3):953-60). Specifically, the constructs bear an antisense DNA oligonucleotide, complementary to the HIV-1 gag RNA sequence, which hybridizes to a complementary RNA oligonucleotide in the dumbbell structure. Upon delivery into the retrovirus-infected cells, cellular RNase H degrades the RNA portion of the dumbbell, thereby releasing the antisense DNA. The liberated antisense molecule then hybridizes to its complementary target viral RNA, thereby invoking RNase H-mediated degradation of the viral RNA strand. While effective at blocking viral proliferation, the mechanism of action of these chimeric dumbbells was designed to target viral gene expression using an antisense mechanism of action and not to inhibit a specific enzymatic function during HIV replication.

Circular dumbbell oligonucleotides have also demonstrated significant biological relevance as aptamers or decoys for hybridizing proteins such as transcription factors (Clusel, et al. (1993) *Nucleic Acids Res.* 21(15):3405-11; Lim, et al. (1997) *Nucl. Acids Res.* 25:575-581) and exhibit relatively high nuclease resistance as well as increased cellular uptake compared to their nicked and linear counterparts (Park, et al. (2000) supra; Yamakawa, et al. (1998) *Bioorg. Med. Chem.* 6(7):1025-32; Yamakawa, et al. (1996) *Nucleosides & Nucleotides* 15:519-529).

Accordingly, there is a need in the art to have reverse transcriptase RNase H inhibitors that exhibit high inhibitory activity and specificity against the RNase H activity of HIV-1 reverse transcriptase without interfering with polymerase function. Furthermore, it is desirable that such inhibitors of RNase H activity are specific for viral RNase H with minimal or no affinity for human ribonucleases.

SUMMARY OF THE INVENTION

One aspect of the present invention is a composition for inhibiting the RNase H activity of a retroid virus reverse transcriptase. The composition is composed of an inhibitory agent of Formula I:

Formula I wherein, $X_1$ and $X_2$ are antiparallel complementary oligonucleotide strands that associate to form a duplex; $X_1$ is 2 to 24 nucleotides in length; and $X_2$ is 2 to 24 nucleotides in length; $Y_1$ and $Y_2$ are 0 to 8 nucleotides in length; at least one of $Y_1$ or $Y_2$ is 2 to 8 nucleotides in length; and $Y_1$ and $Y_2$ each independently contain a ribonucleic acid; 2',5'-linked ribonucleic acid; or a combination thereof and of the sequence 5'-UUYG-3'/2' (SEQ ID NO:1). In one preferred embodiment, $X_1$ and $X_2$ of Formula I are 3',5'-linked ribonucleic acids; deoxyribonucleic acids; 2',5'-linked ribonucleic acids; arabinonucleic acids; 2'-fluoro-arabinonucleic acids locked nucleic acids; peptide nucleic acids; or a combination thereof. In another preferred embodiment, $X_1$ and $X_2$ of Formula I are 3',5'-linked ribonucleic acids and are 4 to 10 nucleotides in length. In a further preferred embodiment, $Y_1$ and $Y_2$ are a 3',5'-linked tetraribonucleotide of the sequence 5'-UUYG-3' (SEQ ID NO:1). In a still further preferred embodiment, a compound of Formula I is a cyclic structure. In a still further preferred embodiment, a compound of Formula I is a hairpin structure.

Another aspect of the present invention is a method for inhibiting the replication of a retroid virus. The method involves contacting a cell infected with a retroid virus with an inhibitory agent of Formula I which inhibits the RNase H activity of the retroid virus reverse transcriptase thereby inhibiting the replication of the retroid virus in said cell.

A further aspect of the present invention is a method for preventing or treating a retroid virus infection. This method involves administering to a subject having or at risk of having a retroid virus infection an effective amount of an inhibitory agent of Formula I which inhibits the RNase H activity of the retroid virus reverse transcriptase so that the replication of the retroid virus is inhibited and the retroid virus infection in said subject is prevented or treated.

DETAILED DESCRIPTION OF THE INVENTION

Eighteen-base pair heteroduplexes which adopt a predominant A-form helical organization (e.g., RNA/RNA or RNA/2',5'-RNA) are capable of binding to the RNase H domain of HIV-1 reverse transcriptase and sequester its ability to degrade the RNA strand in an RNA/DNA hybrid (Wasner, et al. (1998) supra). Although, high affinity binding was observed in vitro, the bimolecular nature of these complexes makes them difficult to develop into effective therapeutics since it is highly unlikely that the complexes would remain in their hybrid state following administration. RNA/RNA and RNA/2',5'-RNA hybrids inhibit *E. coli* RNase H activity, suggesting that these complexes may undesirably impede cellular host RNase H function. Furthermore, the presence of free terminal functional groups renders them susceptible to degradation by ubiquitous cellular nucleases, predominantly of the 3'-exonuclease type (Dolinnaya, et al. (1991) *Nucl. Acids Res.* 19:3067-3072).

As provided herein, combinatorial solid-phase synthesis of oligomeric hairpins having a highly stabile 5'-UUYG-3' (SEQ ID NO:1) tetraloop structure (Hannoush, R. N., Ph.D. Thesis, McGill University, 2002) are effective and specific for the RNase H of HIV-1 reverse transcriptase without affecting the polymerase function of reverse transcriptase or other cellular RNase H activities. The most potent hairpin inhibitors of HIV-1 reverse transcriptase RNase H activity are composed of native RNA hybrid stems and loops displaying $IC_{50}$ values in the range of 7-30 μM., RNA hairpin molecules which adopt global A-type helices are the most potent inhibitors of RNase H activity of HIV-1 reverse transcriptase (Hannoush (2002) supra). These unimolecular complexes display high thermal stability (Hannoush and Damha (2001) *J. Am. Chem. Soc.* 123:12368-12374), however, the presence of free termini make them susceptible to cellular nucleases. Several methods for stabilizing phosphodiester oligonucleotides to biodegradation have been proposed including, incorporation of chemical substituents at the 3'-hydroxyl group (Shaw, et al. (1991) *Nucl. Acids. Res.* 19:747-750), formation of hairpin loop structures at the 3'-end (Tang, et al. (1993) *Nucl. Acids. Res.* 21:2729-2735; Kuwasaki, et al. (1996) *Biochem. Biophys. Res. Comm.* 228(2):623-31), or the intramolecular cyclization of the oligonucleotides through the 3' and 5'-ends (Clusel, et al. (1993) supra). Nucleic acid dumbbells contain termini that are tied up in a circularized structure rendering them resistant to exonucleolytic hydrolysis. Additionally, the high thermal stability of the complexes imparted by the presence of stabilizing loop structures is expected to increase the effective therapeutic concentration of duplexed material upon administration.

Accordingly, one aspect of the present invention relates to a composition composed of an inhibitory agent of the RNase H activity of HIV-1 reverse transcriptase. Said inhibitory agent is a double hairpin oligonucleotide of the structure of Formula I:

Formula I wherein $X_1$ and $X_2$ are two antiparallel complementary oligonucleotide strands that associate to form a duplex (or "stem"), and $X_1$ is a length of 2 to 24 nucleotides, and preferably 4 to 10 nucleotides. $X_2$ is a length of 2 to 24 nucleotides, and preferably 4 to 10 nucleotides. For example, the length of $X_1$ and $X_2$ may be the same so as to favor formation of a perfect duplex; however, it is contemplated that a duplex whereby the length of $X_1=X_2+1$, $X_2=X_1+1$, $X_2=X_1+2$, $X_1=X_2+2$, etc., will also form stable duplexes having a bulging or unpaired nucleotide(s). Preferably, the difference in length between $X_1$ and $X_2$ is not more than 1 or 2 nucleotides so that a stable duplex is formed.

In Formula I of the present invention, $Y_1$ and $Y_2$ are of a length of 0 to 8 nucleotides, preferably 4 nucleotides; at least one of $Y_1$ or $Y_2$ is of a length of 2 to 8 nucleotides, preferably 4 nucleotides; and $Y_1$ and $Y_2$ each independently contain ribonucleic acid (RNA) or 2',5'-linked RNA sequence, or a combination thereof and are of the sequence 5'-UUYG-3'/2' (SEQ ID NO:1), wherein Y is U or C. Preferably, Y represents C. As described herein, a hairpin structure of Formula I is composed of $X_1$ and $X_2$=2 to 24 nucleotides and either $Y_1$ or $Y_2$=0 nucleotides. Similarly, a typical dumbbell structure of Formula I is composed of $X_1$ and $X_2$=2 to 24 nucleotides and $Y_1$ and $Y_2$=2 to 8 nucleotides (i.e., $Y_1$ and $Y_2$>0 nucleotides).

For an inhibitory agent of the present invention containing, for example, the base sequence 5'-TGGAC(UUCG)GUCCA-AAAAC(UUCG)GUUUT-3' (SEQ ID NO:2), the following nomenclature is used: sequences TGGAC (SEQ ID NO:3) and AAAAC (SEQ ID NO:4) represent 5'-stem segments, sequences GUCCA (SEQ ID NO:5) and GUUUT (SEQ ID NO:6) represent 3'-stem segments, wherein the complementary 5' and 3' stem segments anneal and form $X_1$ and $X_2$ of Formula I; and the (UUCG) sequence (SEQ ID NO:7) constitutes the loop (i.e., $Y_1$ and $Y_2$ of Formula I).

Similarly, in a base sequence of 5'-TGGAC(UUCG)GUCCA-3' (SEQ ID NO:8), the sequence TGGAC (SEQ ID NO:3) represents a 5'-stem segment, the sequence GUCCA (SEQ ID NO:5) represents a 3'-stem segment, wherein the complementary 5' and 3' stem segments anneal and form $X_1$ and $X_2$ of Formula I and the (UUCG) sequence (SEQ ID NO:7) constitutes the loop (i.e., $Y_1$ of Formula I and $Y_2$=0).

In the inhibitory agent of Formula I, the dashed line joining $X_1$ and $X_2$ strands represent Watson-Crick base pair interactions. Such base pairings may include, but not be limited to, uracil:adenine (U:A); thymine:adenine (T:A); guanine:cytosine (G:C); 5-methylcytosine:guanine ($^{5Me}$C:G); 5'-substituted pyrimidine:purine base pairs; hypoxanthine:adenine (H:A); H:T; H:C; and the like.

Oligonucleotide strands, represented by $X_1$ and $X_2$ of Formula I, may be composed of, for example, RNA (3',5'-linked); deoxyribonucleic acid (DNA); 2',5'-linked RNA (Giannaris and Damha (1993) *Nucleic Acids Research* 21:4742-4749); arabinonucleic acids (ANA) or 2'-fluoro-ANA (FANA) (see, Damha, et al. (1998) *J. Am. Chem. Soc.* 120:12976; Noronha, et al. (2000) *Biochemistry* 39:7050); locked nucleic acids (LNA) (Rajwansh, et al. (2000) *Angew. Chem. Int. Ed. Engl.* 39:1656-1659); peptide nucleic acids (PNA) (Nielsen, P. E. In: *"Perspectives in Drug Discovery and Design"*, vol. 4, pp. 76, Trainor, G. L. (ed.), ESCOM, Leiden, 1996); or combinations thereof (see, for example entries 12 and 14 of Table 1 having a combination of RNA and DNA residues). See, for example, Sanghvi, Y. S. & Cook, P. D. "Carbohydrate Modifications in Antisense Research" *ACS Symposium Series*, vol. 580. American Chemical Society, Washington DC, 1994 for suitable oligonucleotide backbones. Further, the internucleotide linkages of $X_1$ and $X_2$ may include, but not be limited to, phosphodiester, phosphotriester, phosphorothioate (Eckstein (2000) *Antisense Nucleic Acid Drug Dev.* 10:117-121), methylphosphonate, phosphoramidate (5'N-3'P and 5'P-3'N) groups (Barsky (1997) *Nucleic Acids Res.* 25:830-835), and combinations thereof.

As used herein, when an inhibitory agent of Formula I contains an oligonucleotide strand (i.e., $X_1$ and $X_2$) composed of RNA, said RNA may be substituted at the 2'-position by a fluorine (Manoharan (1999) *Biochim. Biophys. Acta* 1489: 117-130), hydroxyl, amino, azido, alkyl (e.g., methyl, ethyl, propyl, butyl; Nishizaki, et al. (1997) *Biochemistry* 36:2577-2585) or alkoxy (e.g., methoxy, ethoxy, propoxy, or methoxyethoxy; Lind, et al. (1998) *Nucleic Acids Res.* 26:3694-3699) group.

In one embodiment, $X_1$ or $X_2$ of Formula I is an RNA wherein the 2'-substituent is a hydroxyl group.

When an inhibitory agent of Formula I contains an oligonucleotide strand (i.e., $X_1$ and $X_2$) composed of ANA, said ANA may be substituted at the 2'-position by a fluorine, hydroxyl, amino, azido, alkyl (e.g., methyl, ethyl, propyl, butyl), or alkoxy (e.g., methoxy, ethoxy, propoxy, methoxyethoxy) group.

When an inhibitory agent of Formula I contains an oligonucleotide strand (i.e., $X_1$ and $X_2$) composed of 2',5'-linked RNA, said 2',5'-linked RNA may be substituted at the 3'-position by a fluorine, hydroxyl, amino, azido, alkyl (e.g., methyl, ethyl, propyl, butyl), or alkoxy (e.g., methoxy, ethoxy, propoxy, methoxyethoxy) group.

In one embodiment, $X_1$ and $X_2$ of Formula I are each independently a 2',5'-linked RNA.

In a further embodiment, $X_1$ and $X_2$ of Formula I are each independently a 2',5'-linked RNA wherein the 3'-substituent is a hydroxyl group.

Further embodiments of Formula I provide that:
both $X_1$ and $X_2$ are RNA;
both $X_1$ and $X_2$ are 2',5'-linked RNA;
both $X_1$ and $X_2$ are 2'-O-alkyl-RNA;
both $X_1$ and $X_2$ are 2'-alkoxyalkyl-RNA;
both $X_1$ and $X_2$ are 2'-fluoro-RNA;
both $X_1$ and $X_2$ are LNA;
both $X_1$ and $X_2$ are ANA;
both $X_1$ and $X_2$ are FANA;
both $X_1$ and $X_2$ are PNA;
$X_1$ is RNA and $X_2$ is 2',5'-RNA, or vice versa; or
$X_1$ is RNA and $X_2$ is DNA, or vice versa.

In a still further embodiment, both $X_1$ and $X_2$ of Formula I are RNA and are 4 to 10 nucleotide in length.

It is contemplated that in a compound of Formula I either $Y_1$ or $Y_2$, or both $Y_1$ and $Y_2$ may be a 3',5'-linked tetraribonucleotide 5'-UUYG-3' (SEQ ID NO:1); a 2',5'-linked tetraribonucleotide 5'-UUYG-3' (SEQ ID NO:1); a tetraribonucleotide 5'-UUYG-3' (SEQ ID NO:1) containing both 3',5' and 2',5'-linkages (see, for example, entry 15 of Table 1 having both 2',5' and 3',5' linkages: $U_{2'5'}U_{3'5'}C_{3'5'}G_{3'5'}$), or other base compositions or non-nucleotidic linker structure, e.g., polyethylene glycol (PEG), aliphatic linkers, di or tripeptide linkers, dialkyl disulfide linkers, etc.

Exemplary nucleotide sequences for use in generating an inhibitory agent of Formula I include, but are not limited to, GGAC(UUCG)GUCCAAAC(UUCG)GUUU (SEQ ID NO:9), TGGAC(UUCG)GUCCAAAAAC(UUCG)GUUUT (SEQ ID NO:2), and entries 1-40 of Table 1.

It is further contemplated that the inhibitory agents of the present invention may be nicked or ligated to form cyclic structures. Preferably, an inhibitory agent of Formula I is cyclic. In a preferred embodiment, a compound of Formula I is a hairpin structure.

By way of example, a library of compounds of Formula I, wherein $Y_1$=$X_1$=$X_2$=4 nucleotides, and $Y_2$=0 nucleotides, were synthesized on an EXPEDITE™ DNA/RNA synthesizer containing nine monomer reservoirs. This library synthesis took advantage of the presence of only three base-identities in each of the 5'-stem, 3'-stem, and loop regions. DNA, RNA and 2',5'-RNA monomers of each G, C and U (or T) were installed on the gene machine, thus allowing structural diversity-oriented synthesis of a 5'-GUCC-3' (3'-stem; SEQ ID NO:10). The loop was then synthesized via parallel combinatorial synthesis. Subsequently, monomer bottles containing U (or T) were replaced by A (DNA, RNA, and 2',5'-RNA synthesis) and the synthesis of the 5'-GGAC-3' segment (5'-stem; SEQ ID NO:11) was continued to generate 27 hairpin molecules.

By following the same diversity-generating combinatorial approach, 18 other molecules were generated incorporating modifications at specific sites in the hairpin sequence. The library was prepared as a single copy (one CPG-column per library member) on a 1 μmol scale using standard phosphoramidite chemistry with slight modifications, and the individual oligomers were cleaved off the solid support, purified by gel electrophoresis or ion-exchange HPLC, and subsequently characterized by MALDI-TOF mass spectrometry. The overall isolated yields obtained from library solid-phase synthesis were 20-30%. The formation of hairpin species for all library members was verified by the $T_m$ independence of oligonucleotide concentration over at least a 30-fold concentration range, thus confirming a unimolecular folding process for individual library members in solution (0.01 M $Na_2HPO_4$, 0.1 mM $Na_2EDTA$, pH 7.0).

Library members were separated into six different in classes. Table 1 provides library members along their inhibitory constants and thermal melting data.

TABLE 1

| Entry | Code | 5'-Sequence-2'/3'[a] | $IC_{50}$ (μM)[b] | $T_m$ (° C.) | SEQ ID NO: |
|---|---|---|---|---|---|
| 1 | DDD | ggac(uucg)gtcc | — | 56.2 | 12 |
| 2 | DTD | ggac(tttt)gtcc | — | 54.7 | 13 |
| 3 | DRD | ggac(UUCG)gtcc | — | 54.6 | 14 |
| 4 | DRD | ggac(UUCG)gtcc | 96 | 61.4 | 15 |
| 5 | DR¹D | ggac(UACG)gtcc | — | 56.7 | 16 |
| 6 | DR²D | ggac(UUUG)gtcc | 69.1 | 62.0 | 17 |
| 7 | DR³D | ggac(UUUU)gtcc | 97.2 | 54.5 | 18 |
| 8 | RDR | GGAC(uucg)GUCC | — | 63.4 | 19 |
| 9 | RRR | GGAC(UUCG)GUCC | 25.8 | 71.8 | 20 |
| 10 | RRR | GGAC(UUCG)GUCC | 68.9 | 69.3 | 21 |
| 11 | $R_cR_gR$ | GGAc(UUCG)gUCC | >100 | 60.0 | 22 |
| 12 | $R_cR_gR$ | GGAc(UUCG)gUCC | 39.4 | 57.6 | 23 |
| 13 | $R_c$RR | GGAc(UUCG)GUCC | — | 67.3 | 24 |
| 14 | $RR_g$R | GGAC(UUCG)gUCC | 46 | 66.6 | 25 |
| 15 | $RR_U$R | GGAC(UUCG)GUCC | 50.1 | 60.2 | 26 |
| 16 | $R_C$RR | GGAC(UUCG)GUCC | >100 | 62.6 | 27 |
| 17 | $RR_G$R | GGAC(UUCG)GUCC | 98 | 58.0 | 28 |
| 18 | $R_c$RR | GGAC(UUCG)GUCC | — | 61.5 | 29 |
| 19 | $D_CR_GD$ | ggaC(UUCG)Gtcc | — | 59.5 | 30 |
| 20 | $D_CU_GD$ | ggaC(UUUU)Gtcc | — | 51.6 | 31 |
| 21 | $D_CR_GD$ | ggaC(UUCG)Gtcc | — | 52.3 | 32 |
| 22 | $D_CR_GD$ | ggaC(UUCG)Gtcc | — | 57.0 | 33 |
| 23 | DDR | ggac(uucg)GUCC | — | n.d. | 34 |
| 24 | DRR | ggac(UUCG)GUCC | — | 56.5 | 35 |
| 25 | DRR | ggac(UUCG)GUCC | — | 56.7 | 36 |
| 26 | RDD | GGAC(uucg)gtcc | — | n.d. | 37 |
| 27 | RRD | GGAC(UUCG)gtcc | — | 48.1 | 38 |
| 28 | RRD | GGAC(UUCG)gtcc | 47 | 52.8 | 39 |
| 29 | DRR | ggac(UUCG)GUCC | >100 | 24.1 | 40 |
| 30 | DRR | ggac(UUCG)GUCC | 71.4 | 30.2 | 41 |
| 31 | RDR | GGAC(uucg)GUCC | — | n.d. | 42 |
| 32 | RRR | GGAC(UUCG)GUCC | — | 62.6 | 43 |
| 33 | RRR | GGAC(UUCG)GUCC | 58.9 | 62.4 | 44 |
| 34 | RRR | GGAC(UUCG)GUCC | — | 54.1 | 45 |
| 35 | RRR | GGAC(UUCG)GUCC | 42.8 | 58.1 | 46 |
| 36 | RRR | GGAC(UUCG)GUCC | 26.2 | 45.2 | 47 |
| 37 | RRR | GGAC(UUCG)GUCC | 88.5 | 54.8 | 48 |
| 38 | TRT | tttt(UUCG)tttt | — | — | 49 |
| 39 | $R_6RR_6$ | GUGGAC(UUCG)GUCCAC | 7.8 | n.d. | 50 |
| 40 | $R_6RR_6$ | GUGGAC(UUCG)GUCCAC | 29.7 | n.d. | 51 |

[a]Capital letters represent RNA residues; underlined letters are 2',5'-RNA residues (e.g. UC = $U_{2',p5'}C_{2'}p$); DNA residues are represented by small letters; bold letters represent specific point mutations in loop base sequence (entries 5-7) or sugar/phosphodiester composition (entries 11-22).
[b]$IC_{50}$ is the hairpin concentration required to inhibit 50% RNase H activity of HIV-1 reverse transcription and was determined as described herein. Values represent the average of 2 to 3 independent measurements. Errors in $IC_{50}$ values represent standard deviations and were within ±3 μM.
n.d. = $T_m$ was not determined.

The first class (entries 1-4) encompasses DNA hairpins having DNA "D", RNA "R" and 2',5'-RNA "R" loops. The second class (entries 5-7) was designed to test the effect of loop base sequence on the inhibitory properties of DRD hairpins. The third class (entries 8-10) is similar to the first class, but contains RNA residues in the stem region. The fourth class (entries 11-22) encompasses hairpins that are derivatives of the first or third class that contain one or two sugar-phosphate backbone modifications while keeping the base sequence unchanged. The fifth class (entries 23-38) was designed to test the effects of the stem (DD, RR, RR, DR, D R, or RR) on the inhibition of RNase H activity. Further, the sixth class (entries 39 and 40) was designed to test the effect of stem length on inhibition of RNase H activity.

Hairpin molecules were screened for their ability to act as potential inhibitors of HIV-1 reverse transcriptase RNase H activity. The inhibition assay used a 5'-[$^{32}$P]-labeled RNA oligonucleotide (18-mer) that was annealed to a complementary unlabeled DNA strand. The resulting 5'-[$^{32}$P]-RNA:DNA hybrid duplex was then incubated with HIV-1 reverse transcriptase in either the absence or presence of variable amounts of hairpins at 37° C. The ability of various hairpins to inhibit HIV-1 reverse transcriptase RNase H-mediated degradation of the 5'-$^{32}$P-labeled RNA strand in the RNA:DNA hybrid was measured by gel densitometric analysis as judged from the disappearance of the full-length RNA substrate and/or the appearance of the smaller degradation products. The $IC_{50}$ value, defined as the hairpin concentration required to inhibit 50% of RNase H-mediated RNA degradation in the RNA:DNA hybrid, was calculated from plots of the residual undegraded 5'-[$^{32}$P]-RNA versus hairpin concentration.

The degree of inhibition varied with loop and stem compositions. Hairpins composed of DNA loops were not able to inhibit RNase H activity regardless of hairpin stem composition. For example, hairpins DDD, RDR, DDR, and RDR, all containing DNA residues in the loop, showed no inhibition of HIV-1 reverse transcriptase RNase H-mediated degradation of RNA in the RNA:DNA hybrid.

Conversely, hairpins containing either R or R loops showed various degrees of inhibition depending on hairpin stem composition. $IC_{50}$ values were in the 7.8-100 µM range. The hairpin RRR was a potent inhibitor of HIV-1 reverse transcriptase RNase H activity with an $IC_{50}$ of 25.8 µM. Replacing the loop with 2',5'-RNA [RRR] resulted in an increase in $IC_{50}$ to 68.9 µM. Among members of the fourth class, the most potent was $R_gR_gR$ [i.e., 5'-GGAc(UUCG)gUCC-3'; SEQ ID NO:23; $IC_{50}$=39.4 µM]. Of note, RRR was the most potent among members of the fifth class with an $IC_{50}$ similar to that of RRR (~26 µM). Hairpins RRD and RRR (entries 28 and 35) were also excellent inhibitors of HIV-1 reverse transcriptase RNase H activity with almost similar $IC_{50}$ values (~45 µM). In contrast, the corresponding hairpins with 3',5'-RNA loops, i.e., RRD and RRR, showed little inhibition of HIV-1 reverse transcriptase RNase H activity.

Increasing stem length resulted in a significant increase in inhibitory activity. The hairpin $R_6RR_6$ (with 6 base pairs in the stem, $IC_{50}$=7.8 µM) was approximately three times more potent than RRR, while $R_6RR_6$ ($IC_{50}$~30 µM) was two times more potent than RRR [$IC_{50}$~69 µM]. Thus, the RNA hairpin $R_6RR_6$ was the most potent HIV-1 reverse transcriptase RNase H inhibitor among library members.

In addition to exemplary compounds of Formula I as provided in Table 1, RNA double tetraloop compounds of Formula I were synthesized. These compounds are also referred to herein as double hairpin or dumbbell-shaped structures of Formula I. Nicked compounds were synthesized on an ABI 381A DNA synthesizer using standard silyl phosphoramidite chemistry and reagents. A 5'-UUCG-3' (SEQ ID NO:7) loop sequence provided a rigid structural moiety (Cheong, et al. (1990) Nature 346:680-682; Varani, et al. (1991) Biochemistry 30:3280-3289) to the nicked RNA double tetraloop compounds of Formula I and may be a key recognition motif for effective binding to the RNase H domain of HIV-1 reverse transcriptase (Hannoush (2002) supra). Compounds were purified by denaturing PAGE (8.3 M urea), desalted by SEC and their nucleotide composition confirmed by MALDI-TOF-MS.

Chemical ligation of the nicked phosphate and hydroxyl junction to produce a cyclic double-helical structure was achieved using cyanogen bromide (CNBr) as a condensing agent. The extent of ligation in each of the double tetraloop oligonucleotides was monitored by denaturing PAGE and/or reverse-phase HPLC. The nature of the nucleotide residues facing the nicked junction is critical for high yield cyclization (Merenkova, et al. (1993) Bioorg. Khim. 19:1205-1214; Merenkova, et al. (1992) Bioorg. Khim. 18:85-91). When a 5'-rG/3'-p(rU) was incorporated at the ligation juncture to produce the compound designated 4.1 ($^{HO}$GGAC(UUCG)GUCCAAAC(UUCG)GUUU$_P$; SEQ ID NO:9), no cyclization was observed based on the absence of any new product species on the 16% denaturing gel. Higher crosslinked gels (i.e., 20 and 24%) also confirmed that ligation did not take place. This indicated that the phosphate and hydroxyl groups were not appropriately aligned for condensation to take place. Not wishing to be bound by theory, this may have been due to the predominant C3'-endo conformation adopted by the ribonucleoside units at the terminal positions. Thus, the 3'-phosphate would be placed in a pseudoequatorial arrangement, which may sterically hinder its interaction with the neighboring hydroxyl group. Furthermore, since the 3'-phosphate was adjacent to a reactive 2'-hydroxyl in the ribonucleotide unit, intramolecular 2',3'-cyclophosphate formation may have occurred upon CNBr activation (Dolinnaya, et al. (1991) supra). This would potentially lead to a mixture of 2',5' and 3',5'-phosphodiester linkages at the ligation site. However, if the correct local geometry for effective ligation was not achieved, then water would compete with the 5'-hydroxyl for the cyclophosphate, and reversion to the 2' or 3'-phosphate termini would predominate. Given the lack of any new product species, it appeared that the latter prevailed.

Terminal ribonucleotide units were substituted with a more productive 5'-T/3'-pT deoxynucleotide nicked junction. As a result, intramolecular cyclization proceeded to afford a 77% yield of the cyclized double tetraloop compound designated 4.2 ($^{HO}$tGGAC(UUCG)GUCCAAAAAC(UUCG)GUUUt$_P$; SEQ ID NO:2) indicating that the reactive phosphate and hydroxyl units were in the correct stereogeometry for effective ligation. Similar to DNA dumbbells, the circularized dumbbell displays an accelerated electrophoretic mobility compared to its nicked counterpart, likely due to its more compact and globular structure. The new product band was excised from the gel, soaked in water overnight and desalted by SEC. Chromatographic analysis of the ligation mixture by reverse-phase HPLC further demonstrated successful cyclization. As a result of its more spherical and compressed structure, the closed, circular product had a slightly faster retention time when compared to its nicked counterpart.

Subsequently, the nicked and circularized double tetraloop compounds were chemically characterized. Thermal denaturation analysis of the nicked complexes (Table 2) indicated that the intramolecular dumbbell structures of compounds 4.1 and 4.2 melted with biphasic profiles. Under identical buffer conditions (10 mM $Na_2HPO_4$, 0.1 mM $Na_2EDTA$, pH 7.0), the acyclic tetraloop exhibited similar $T_m$ transitions as two previously studied independent hairpin structures (Table 1), which constituted the nicked dumbbell 4.1 ($^{HO}$GGAC(UCG)GUCCAAAC(UUCG)GUUU$_P$; SEQ ID NO:9). The large disparity in $T_m$ (>30° C.) between the left and right portions of the nicked dumbbells was attributed to one half being comprised of a more thermally stable rG-rC rich stem, whereas the other bisection included an abundant rA-rU hybrid region. The closed, circular nature of ligated dumbbell 4.2 ($^{HO}$tGGAC(UUCG)GUCCAAAAAC(UUCG)GUUUt$_P$; SEQ ID NO:2) was further confirmed by monitoring its $T_m$ profile. The ligated or cyclic oligonucleotides displayed a cooperative, unimolecular order-disorder transition that was significantly higher than the independent transitions observed for the open dumbbell complex. MALDI-TOF-MS analysis of the pure ligated product exposed a molecular weight consistent with the loss of a water molecule, indicating that the phosphate/hydroxyl junction had been sealed off in the form of a new phosphodiester linkage.

The RNase H activity of the double hairpin compounds 4.1 ($^{HO}$GGAC(UUCG)GUCCAAAC(UUCG)GUUU$_P$; SEQ ID NO:9) and 4.2 ($^{HO}$tGGAC(UUCG)GUCCAAAAAC(UUCG)GUUUt$_P$; SEQ ID NO:2) were tested for inhibition of the RNase H activity of HIV-1 reverse transcriptase, and their activity was compared to potent RNA single hairpin inhibitors of Table 1.

Initially, a 5'-[$^{32}$P]-terminally radiolabeled RNA oligonucleotide (18-nucleotides) was annealed to its complementary DNA strand to form a 5'-[$^{32}$P]-RNA/DNA hybrid. The resultant duplex was treated with HIV-1 reverse transcriptase (p66/p51 heterodimer), which had been pre-incubated with variable concentrations of RNA double hairpins. The extent of inhibition of the HIV-1 reverse transcriptase RNase H-mediated degradation of the 5'-[$^{32}$P]-labeled RNA strand in the heteroduplex by the nicked or ligated double hairpin RNA oligonucleotide was measured by densitometric analysis as assessed from the depreciation of the full-length RNA substrate. The IC$_{50}$ value (Table 2) was calculated from a plot of the outstanding undegraded 5'-[$^{32}$P]-RNA versus the concentration of hairpin RNA oligonucleotide.

scriptase RNase H-mediated degradation of the RNA strand. Nonetheless, the activity of the RNA double hairpin 4.2 maintained nearly double the potency of hairpin HP-L. The combined results indicate that stem-length is an important factor in designing more potent inhibitors of the RNase H activity of HIV-1 reverse transcriptase. The most potent inhibitor; the closed, double hairpin structure 4.2, comprises eight base-paired nucleotides in the stem, indicating that longer RNA/RNA duplexes may be better accommodated in the RNase H domain of HIV-1 reverse transcriptase. Studies with RNA hairpin structures suggest that HIV-1 reverse transcriptase

TABLE 2

| Compound | Sequence (5'→3') | $T_m$ (° C.) | IC$_{50}$ (μM) | SEQ ID NO: |
|---|---|---|---|---|
| HP-S1$^a$ | $^{HO}$GGAC(UUCG)GUCC$_{OH}$ | 71.8 | 25.8 | 18 |
| HP-S2$^a$ | $^{HO}$AAAC(UUCG)GUUU$_{OH}$ | 52.4 | — | 52 |
| HP-L$^a$ | $^{HO}$GUGGAC(UUCG)GUCCAC$_{OH}$ | n.d. | 7.8 | 50 |
| 4.1 | $^{HO}$GGAC(UUCG)GUCCAAAC(UUCG)GUUU$_P$ | 44.1, 79.7 | >60 | 9 |
| 4.2 (N) | $^{HO}$tGGAC(UUCG)GUCCAAAAAC(UUCG)GUUUt$_P$ | 43.0, 76.6 | 40.4 | 2 |
| 4.2 (L) | $^{HO}$tGGAC(UUCG)GUCCAAAAAC(UUCG)GUUUt$_P$ | 87.0 | 3.3 | 2 |

$^a$Hairpin values were obtained from Table 1.
$T_m$ values for nicked and ligated dumbbells represent the average of three successive runs and are within ±0.5° C. (Buffer: 10 mM Na$_2$HPO$_4$, 0.1 mM Na$_2$EDTA, pH 7.0).
The IC$_{50}$ value is the amount of dumbbell or hairpin molecule required to inhibit the HIV-1 reverse transcriptase RNase H-mediated degradation of a substrate DNA/RNA hybrid by 50%.
IC$_{50}$ values are the average of 2-3 independent measurements. The error associated with the IC$_{50}$ is represented by a standard deviation of ±1 μM.
RNA residues are represented by capital letters whereas small letters indicate DNA residues. Bracketed residues designate the stabilizing hairpin loop base sequence.
OH = terminal hydroxyl; P = terminal phosphate; N = nicked dumbbell; L = ligated dumbbell.

Although the loop sequence was identical in both nicked and cyclized RNA double hairpin compounds 4.1 and 4.2, the degree of inhibition appeared to correlate directly with stem length (4+4 versus 5+5 base pairs). Increasing the length of the stem by one base pair in each bisection more than doubled the potency of the open dumbbell structure of 4.2 compared to 4.1 (Table 2). A similar trend was apparent in the RNA hairpin structures, wherein the stem was composed of six base pairs (HP-L) rather than four base pairs (HP-S1), resulting in a nearly three-fold enhancement in potency. In addition, the most potent hairpin structure (HP-L) demonstrated at least five times the inhibitory activity of the nicked dumbbell compound 4.2. The cyclic double hairpin structure 4.2 (IC$_{50}$=3.3 μM) was more than ten times more potent than its nicked counterpart (IC$_{50}$=40.4 μM). A direct comparison of the inhibitory activity of HP-L and ligated 4.2 revealed that the cyclic RNA double hairpin was at least two-fold more active than the hairpin structure under identical reaction conditions. Whether this effect was dependent on the length of the stem region alone, or on the presence of two, rather than one UUCG loop motif (SEQ ID NO:7) was not determined. At a low concentration of inhibitor (i.e., 5 μM), neither the nicked form of 4.2 nor the most potent short RNA hairpin structure (HP-S1) displayed any inhibitory activity. Conversely, both the longer RNA hairpin (HP-L) and the ligated RNA double hairpin (4.2) effectively inhibited the HIV-1 reverse trandistinguishes and recognizes the unusually folded UUCG loop structure (SEQ ID NO:7) as a signal for binding to its substrate. Further, mutating the loop region sequence of UUCG (SEQ ID NO:7) to UACG (SEQ ID NO:53) of RNA hairpins completely abolishes hairpin activity. Incorporating a second stabilizing loop motif by creating a double-hairpin structure did not increase the inhibitory potency, rather, biological activity was severely compromised (Table 1; compare HP-S1 to nicked dumbbells 4.1 and 4.2). In contrast, the ligated double hairpin 4.2, which also contained two UUCG loop motifs (SEQ ID NO:7), was the most potent of all the molecules examined. Not wishing to be bound by theory, this indicates that HIV reverse transcriptase requires only one loop structure for ample recognition and binding, but a longer stem region is requisite for grasping and positioning the substrate within its binding domain. Moreover, the second loop motif may play an essential role in vivo, by stabilizing the structures against the ever-prominent exonucleases present in the biological milieu.

Several HIV-1 reverse transcriptase RNase H inhibitors of the art such as RNA/RNA and RNA/2',5'-RNA hybrids, as well as the natural product illimaquinone, inhibit HIV-1 reverse transcriptase RNase H as well as E. coli RNase H activity, suggesting that such molecules may undesirably obstruct cellular RNase H activity. Thus, it was determined whether the inhibitory agents of the present invention demonstrate a selectivity for the RNase H domain of HIV-1 reverse transcriptase. Heteroduplexes used in the inhibition profiles described herein (i.e., 5'-[$^{32}$P]-RNA/DNA heteroduplexes) were incubated with *E. coli* RNase H or human RNase H (type II) in either the presence or absence of cold hairpin (HP-L) or ligated RNA double hairpin (4.2) inhibitors. RNase H inhibition was determined by comparing the amount of intact RNA present in reactions containing or lacking inhibitor. Formerly, the RNA hairpin structure HP-L demonstrated no specificity towards either homolog of RNase H. This was reproducibly confirmed in the assay conducted herein. Similarly, RNA dumbbell 4.2 did not effect either the bacterial or human RNase H-mediated degradation of the RNA template strand, indicating a remarkably specific effect toward the retroviral RNase H domain.

To confirm that the inhibitory agents of the present invention bind specifically to the RNase H domain of HIV reverse transcriptase, UV-crosslinking experiments were conducted using cyclic compound 4.2 and either the HIV-1 reverse transcriptase heterodimer (p66/p51), containing both the DNA polymerase and RNase H domains, or the homodimer (p51/p51) consisting of only a functional DNA polymerase domain. The p66 monomeric subunit of HIV-1 reverse transcriptase is preoteolytically processed to form both a p51 and p15 subunit, resulting in an RNase H deficient product (Schatz, et al. (1989) *FEBS Lett.* 257:311-314). In the virion particle, p66 is always found in stable association with the p51 subunit, and it is this resultant heterodimeric entity that displays the full functionality of the HIV-1 reverse transcriptase (Hansen, et al. (1988) *EMBO J.* 7:239-243; Starnes and Cheng (1989) *J. Biol. Chem.* 264:7073-7077). By taking advantage of the natural photoreactivity of the RNA bases at 254 nm, it is possible to form a cross-linked complex between inhibitor aptamers and the RNase H domain of HIV reverse transcriptase located in the C-terminal portion of the p66 subunit. The complex exhibits altered electrophoretic mobility compared to its unbound state. However, in the case of the RNA dumbbells, both the 5' and 3'-termini of the molecule are engaged in a circularized structure, so introduction of a terminal radiolabel was not feasible. Alternatively, complex formation may also be discerned by monitoring a change in the electrophoretic mobility of the protein subunits themselves on a denaturing sodium dodecyl sulfate (SDS) gel followed by staining of the protein complex.

Thus, ligated RNA double hairpin 4.2 was incubated with either the fully functional p66/p51 HIV-1 reverse transcriptase dimer or the RNase H-deficient p51/p51 dimer for a 30-minute period at 37° C. The oligonucleotide-enzyme mixtures were placed on ice to stabilize the complex and irradiated with UV light ($\lambda$=254 nm) for 15 minutes. Complexes were then partitioned on a 12% SDS-PAGE and stained. The results demonstrated that the circular RNA dumbbell did not form a covalent complex with the p51/p51 homodimer, which lacks the RNase H binding domain. Since the p51/p51 homodimer possesses functional DNA polymerase activity, it is expected that if the RNA dumbbell recognizes this domain, then a stable adduct would form. In contrast, aggregate formation with the p66/p51 heterodimeric species was evident, as the presence of a slower migrating product complex on the SDS-PAGE was observed. Moreover, the covalent complex formed between the p66 subunit and the ligated RNA dumbbell exhibited a molecular weight consistent with the predicted molecular weight of ca. 75 KDa. These findings demonstrate that the RNA dumbbell aptamer 4.2 does not bind the DNA polymerase region of HIV-1 reverse transcriptase, and instead, is highly specific toward the RNase H domain of the enzyme. Furthermore, the RNA dumbbell 4.2 does not have any effect on the HIV-1 reverse transcriptase-mediated synthesis of DNA by DNA-dependent DNA polymerase or RNA-dependent DNA polymerase activities. It is contemplated that the RNA dumbbell may bind the active site of the enzyme (competitive inhibition) or bind a secondary site (non-competitive inhibitor) thereby inducing an allosteric change in the enzyme active site.

As demonstrated herein, the RNase H activity of a retroid virus reverse transcriptase was effectively inhibited by acyclic and cyclic double hairpin compounds without affecting the polymerase activity of the retroid virus reverse transcriptase or other cellular RNase H enzymes. As the RNase H domain of the retroid virus reverse transcriptase is essential for retroid virus replication, a further aspect of the present invention is a method for inhibiting the replication or proliferation of a retroid virus using an inhibitory agent of Formula I. This method of the invention involves contacting a cell infected with a retroid virus with an effective amount of an inhibitory agent of Formula I so that the RNase H activity of the retroid virus reverse transcriptase is inhibited or reduced thereby inhibiting or reducing retroid virus proliferation or replication as compared to a cell infected with a retroid virus which has not been contacted with an inhibitory agent of Formula I. It is contemplated that this method of the present invention may be useful in preventing or treating a retroid virus infection or modulating the replication of a retroid virus vector used in gene therapy (Pan et al. (2002) Mol. Ther. 6(1):19-29).

In general, an inhibitory agent of Formula I may be one component of a pharmaceutical composition. Preferably, the pharmaceutical composition or pharmaceutical preparation contains an efficacious dose of at least one compound of Formula I and a pharmaceutically acceptable carrier. Further, the pharmaceutical composition may contain a mixture of compounds of Formula I and a pharmaceutically acceptable carrier. The pharmaceutical composition may be administered orally, for example in the form of pills, tablets, lacquered tablets, coated tablets, granules, hard and soft gelatin capsules, solutions, syrups, emulsions, suspensions or aerosol mixtures. Administration may also be carried out rectally (e.g., in the form of a suppository); parenterally (e.g., intravenously, intramuscularly, subcutaneously in the form of injection solutions or infusion solutions, microcapsules, implants or rods); or percutaneously or topically (e.g., in the form of ointments, solutions, emulsions or tinctures, aerosols, nasal sprays, patches, bandages or liquid bandages).

The selected pharmaceutically acceptable carrier may be dependent on the route of administration and may be an inert inorganic and/or organic carrier substance and/or additive. For the production of pills, tablets, coated tablets and hard gelatin capsules, the pharmaceutically acceptable carrier may include lactose, corn starch or derivatives thereof, talc, stearic acid or its salts, and the like. Pharmaceutically acceptable carriers for soft gelatin capsules and suppositories include, for example, fats, waxes, semisolid and liquid polyols, natural or hardened oils, and the like. Suitable carriers for the production of solutions, emulsions, or syrups include, but are not limited to, water, alcohols, glycerol, polyols, sucrose, glucose, and vegetable oils. Suitable carriers for microcapsules, implants or rods include copolymers of glycolic acid and lactic acid.

A pharmaceutical composition, in general, contains about 0.5 to 90% by weight of an inhibitory agent of Formula I. The amount of active ingredient of Formula I in the pharmaceutical composition normally is from about 0.2 mg to about 1000 mg, preferably from about 1 mg to about 500 mg.

In addition to an inhibitory agent of Formula I and a pharmaceutically acceptable carrier, the pharmaceutical composition may contain an additive or auxiliary substance. Exemplary additives include, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. A generally recognized compendium of methods and ingredients of pharmaceutical compositions is Remington: The Science and Practice of Pharmacy, Alfonso R. Gennaro, editor, 20th ed. Lippingcott Williams & Wilkins: Philadelphia, Pa., 2000. Furthermore, one or more other pharmaceutically active agent (e.g., Docosano; antiretroviral agents such as Efavirenz, Didanosine, Lamivudine, Indinavir, Stavudine, Nelfinavir, Ritonavir, Zidovudine, Lopinavir, Saquinavir, Abacavir, Zalcitabine, Amprenavir, Delavirdine, Nevirapine, Tenofovir, Zalcitabine; alpha interferon, reverse transcriptase inhibitors and the like) may be formulated in the pharmaceutical composition of the invention to enhance the desired effect of inhibiting, reducing, or stabilizing retroid virus proliferation or replication.

Accordingly, a further aspect of the present invention is a method of preventing or treating a retroid virus infection by administering to a subject having or at risk of having a retroid virus infection an effective amount of an inhibitory agent of Formula I or pharmaceutical composition containing an inhibitory agent of Formula I. A subject at risk of having or suspected of having a retroid virus infection is an individual who may have, for example, had a blood transfusion suspected of being contaminated with a retroid virus. A subject having a retroid virus infection may include an individual exhibiting signs or symptoms of a retroid virus infection including high viral loads.

An effective amount of an inhibitory agent of Formula I is considered an amount which inhibits, reduces, or stabilizes at least one sign or symptom associated with a retroid virus infection. Signs or symptoms which may be evaluated to determine the effectiveness of a compound or composition of the invention include, but are not limited to, viral load as determined by well-known methods such as quantitative RT-PCR, northern blot analysis, determining RNase H activity, measuring cell-associated viral capsid protein, and the like. Further, as CD4+ T cell responses are generally related to the degree of viral load suppression, these responses may also be measured. Individuals who have benefited from a compound or composition of the present invention may exhibit a low baseline viremia and high baseline CD4+ T cell count, and a rapid decline of viremia.

Those of ordinary skill in the art may. readily optimize effective doses and co-administration regimens as determined by good medical practice and the clinical condition of the individual patient. Regardless of the manner of administration, it may be appreciated that the actual preferred amounts of active compound in a specific case will vary according to the efficacy of the specific compound employed, the particular compositions formulated, and the route of administration. The specific dose for a particular patient depends on age, body weight, general state of health, on diet, on the timing and route of administration, on the rate of excretion, and on medicaments used in combination and the severity of the particular disorder to which the therapy is applied. Dosages for a given subject may be determined using conventional considerations, e.g., by customary comparison of the differential activities of the subject compounds and of a known agent, such as by means of an appropriate conventional pharmacological protocol. Generally, an amount between 0.1 mg/kg and 100 mg/kg body weight/day of active ingredient is administered dependent upon potency of the inhibitory agent of Formula I.

Compounds and pharmaceutical compositions provided herein are useful in preventing or treating a retroid virus infection via decreasing or inhibiting the proliferation or replication of a retroid virus, more preferably the retroid virus is a retrovirus, most preferably human immunodeficiency virus in a mammalian subject including humans, pets, farm animals, and zoo animals. Exemplary retroid viruses include, but are not limited to, Hepadnaviruses (e.g., Arctic ground squirrel hepatitis B virus, Duck hepatitis B virus, Ground squirrel hepatitis virus, Hepatitis B virus, Heron hepatitis B virus, Orangutan hepadnavirus, Stork hepatitis B virus, Woodchuck hepatitis B virus, Woolly monkey hepatitis B Virus) and retroviruses (e.g., Abelson murine leukemia virus, Avian leukosis virus, Avian myelocytomatosis virus, Avian sarcoma virus, Avian sarcoma virus Y73, Bovine foamy virus, Bovine immunodeficiency virus, Bovine leukemia virus, Caprine arthritis-encephalitis virus, Caprine nasal tumor virus, Equine foamy virus, Equine infectious anemia virus, Feline foamy virus, Feline immunodeficiency virus, Feline leukemia virus, Friend murine leukemia virus, Fujinami sarcoma virus, Gibbon ape leukemia virus, Human foamy virus, Human immunodeficiency virus 1, Human immunodeficiency virus 2, Human spumaretrovirus, Human T-lymphotropic virus 1, Human T-lymphotropic virus 2, Jembrana disease virus, Mason-Pfizer monkey virus, Moloney murine sarcoma virus, Mouse mammary tumor virus, Murine leukemia virus, Murine osteosarcoma virus, Murine sarcoma virus, Murine type C retrovirus, Ovine lentivirus, Ovine pulmonary adenocarcinoma virus, Porcine endogenous retrovirus, Primate T-lymphotropic virus 3, Rauscher murine leukemia virus, Rous sarcoma virus, Simian foamy virus, Simian immunodeficiency virus, Simian immunodeficiency virus 2, Simian T-lymphotropic virus 1, Simian T-lymphotropic virus 2, Simian-Human immunodeficiency virus, Snakehead retrovirus, Spleen focus-forming virus, Visna virus, Walleye dermal sarcoma virus, Woolly monkey sarcoma virus).

A further aspect of the present invention is to provide the oligonucleotides of Formula I for diagnostic applications such as radiolabeled reagents. Suitable radiolabels include, but are not limited to, $C^{14}$, $P^{32}$, $H^3$, $S^{35}$, $O^{18}$ and $F^{19}$ which may be incorporated by means known to those skilled in the art. The oligonucleotides of Formula I may also contain fluorescent labels, such as fluorescein, rhodamine or may be biotinylated. When modified in this way, the oligonucleotides are particularly useful as in vivo or in vitro diagnostic agents.

The invention is described in greater detail by the following non-limiting examples.

EXAMPLE 1

Solid-Phase Synthesis of Oligonucleotides

Synthesis of linear and branched oligonucleotides was conducted on an Applied Biosystems (ABI, Foster City, Calif.) 381A synthesizer using the standard β-cyanoethyl phosphoramidite chemistry and the 1 μmol scale delivery cycle supplied by the manufacturer with slight modifications. The standard cycle was customized to include the following: (1) phosphoramidite coupling: the coupling time or "wait" step was extended to 120 seconds for the 2'-deoxyribonucleoside phosphoramidites (dA, dC, dT) and 240 seconds for dG, as well as 450 seconds for the ribonucleoside phosphoramidites (rA, rC, rU) and 600 seconds for rG, (2) capping: acetylation of unreacted 5'-hydroxyl groups was accomplished by a 17 second delivery of Cap A and Cap B reagent followed by a 45 second "wait" step and repeated, (3) oxidation: oxidant solution was delivered to the column for 20 seconds followed by a 20 second "wait" step (4) detritylation: solution of 3% trichloroacetic acid (TCA) in 1,2-dichloroethane (DCE) was continuously delivered for 120 seconds to the column for the removal of DMT-containing groups.

Preceding the assembly of the oligonucleotide chain, the nucleoside-derivatized solid support (1 μmol controlled-pore glass (CPG)) was packed into an empty synthesizer column (ABI), installed on the instrument and treated with a mixture of Cap A and Cap B reagents according to the pre-installed "capping" cycle provided by ABI. This step ensured that any undesired hydroxyl or amino groups on the CPG surface were masked by acetylation (Damha, et al. (1990) *Nucleic Acids Res.* 18:3813-3821), and also eliminated any trace moisture at the beginning of the synthesis. Phosphoramidite reagents were dissolved in freshly distilled acetonitrile, which was introduced via dry syringe through the septum of a sealed amber glass bottle containing the appropriate monomer. The final concentrations of the conventional monomers were 0.1 M for the 2'-deoxyribonucleoside phosphoramidites and 0.15 M for the ribonucleoside phosphoramidites unless otherwise noted. Working concentrations of any atypical nucleoside and non-nucleoside phosphoramidites are provided herein. Monitoring of successive coupling efficiencies was conducted by measuring the absorbance (at 505 nm) of the trityl cation released during the TCA treatment step.

EXAMPLE 2

Acid Activation and Succinylation of the CPG

Long-chain alkylamine CPG (LCAA-CPG) was activated and succinylated according to well-established methods (Damha, et al. (1990) supra; Pon, et al. (1988) *Biotechniques* 6:768-775). LCAA-CPG (4 grams, 500 Å or 1000 Å pore size) (Dalton Chemical Laboratories, Toronto, Canada) was treated with a solution of 3% TCA in DCE (w/v) for 24-48 hours at room temperature in order to liberate a maximal number of reactive amino sites on the support surface. The activated CPG was filtered and neutralized by washing with 9:1, triethylamine:DIPEA (50 mL), washed successively with dichloromethane and diethyl ether, and placed in a vacuum dessicator to dry (12-24 hours) prior to succinylation.

The acid-activated LCAA-CPG (1 gram), succinic anhydride (2 mmol, 0.20 gram) and 4-DMAP (0.33 mmol, 40 mg) were placed in a septum-sealed 10 mL glass vial. Anhydrous pyridine (6 mL) was added via syringe and the vial shaken gently at room temperature for 24 hours. The contents were filtered and washed sequentially with pyridine, dichloromethane and diethyl ether and placed in a vacuum dessicator over phosphorus pentoxide to dry.

EXAMPLE 3

Nucleoside Derivatization of CPG

Method A (Average Loading: 25-50 μmol/g). CPG loadings of all deoxyribonucleoside and ribonucleosides which were acceptable for the synthesis of linear oligonucleotides (<50 nucleotides=500 Å CPG, >50 nucleotides=1000 Å CPG) were attained using the coupling reagents DEC and DMAP according to standard methods (Damha, et al. (1990) supra). Briefly, succinylated LCAA-CPG (0.5 gram), 5'-O-dimethoxytrityl-N-protected nucleoside (0.1 mmol), 4-DMAP (0.05 mmol, 6 mg) and DEC (1.0 mmol, 192 mg) were placed into a septum-sealed 10 mL glass vial. Anhydrous pyridine (6 mL) and triethylamine (40 μL) were added and the mixture shaken for 24 hours at room temperature. The CPG was isolated by vacuum filtration, washed with dichloromethane and ether and dried in vacuo overnight. The amount of nucleoside loaded onto the support was determined by measuring the absorbance of the trityl cations (DMT$^+$) released from an accurately weighed amount of CPG upon treatment with 3% TCA in DCE. Prior to chain assembly on an oligonucleotide synthesizer, any free amino or hydroxyl groups present on the support were acetylated in order to "cap" any potential reactive sites.

Method B (Controlled and High Loading CPG). Method B was carried out according to well-established methods (Pon, et al. (1999) *Bioconj. Chem.* 10:1051-1057). The rapid derivatization of controlled loadings of nucleoside (e.g., low nucleoside loadings: 5-10 μmol/g) and high loading supports (≈90 μmol/g) was attainable when the condensing reagents used were a mixture of either HATU or HBTU and 4-DMAP. When a specific loading of nucleoside was desired (e.g., 10 μmol/g), then a limiting amount (15-20 μmol) of nucleoside/gram (i.e., 15-20 μmol/g) of succinylated CPG was used. When maximal loading was desired (e.g., 90 μmol/g) then an excessive amount of nucleoside/gram (400 μmol/g) of CPG was used. The conditions for the derivatization of a high-loading CPG were as follows: succinylated LCAA-CPG (0.25 gram), HATU or HBTU (0.1 mmol), 5'-O-DMT-N-protected nucleoside (0.1 mmol) and 4-DMAP (12 mg) were added to a septum-capped 10 mL glass vial. The coupling reaction was initiated by the addition of acetonitrile (1-2 mL) and the contents left shaking at room temperature for 2 hours. The CPG was filtered and washed successively with dichloromethane, methanol and ether and dried in vacuo overnight. Nucleoside loading was determined by trityl cation release from the CPG surface upon treatment with a known volume of 3% TCA in DCE. The absorbance reading of the trityl cation (DMT$^+$) was measured at 505 nm. CPG was "capped" on the oligonucleotide synthesizer prior to chain assembly.

EXAMPLE 4

Cleavage from CPG and Deblocking of Protecting Groups

CPG-bound oligonucleotides were transferred to a 1.5 mL microtube and suspended in 3:1 (v/v) aqueous ammonia (29%)/absolute ethanol and gently shaken at room temperature for 24 hours (48 hours for those sequences containing N$^2$-(i-Bu)-guanine) to cleave the oligonucleotide from the support and deblock any phosphate and base protecting groups. The supernatant was removed, the CPG washed with ethanol (3×0.5 mL) and the fractions dried in a SPEED-VAC® concentrator under a low (house) vacuum.

Given that RNA oligonucleotides bear an extra 2'-TBDMS protecting group, such molecules were consequently treated with the desilylating reagent, TREAT-HF (5 μL/crude A$_{260}$ unit) for 48 hours at room temperature (Gasparutto, et al. (1992) *Nucl. Acids Res.* 20:5159-5166). The solution was then either quenched with sterile water (1 mL) and dried, or precipitated directly from the desilylation reaction by adding 25 μL of 3 M sodium acetate (pH 5.5) followed by 1 mL of cold n-butanol (Sproat, et al. (1995) *Nucleosides & Nucleotides* 14:255-273). The precipitated material was centrifuged at maximum speed for 10 minutes and the RNA pellet was washed with 70% ethanol (2×0.5 mL) and dried. Alternatively, the 2'-O-TBDMS group was removed using a mixture of TREAT-HF and N-methylpyrrolidinone (NMP; Aldrich, St. Louis, Mo.) according to standard methods (Wincott, et al. (1995) *Nucl. Acids Res.* 23:2677-2684). Briefly, the crude, silylated RNA was suspended in 6:3:4 (v/v/v) NMP/triethylamine/TREAT-HF (250 µL), heated to 65° C. for 1.5 hours and precipitated with n-butanol as described herein.

EXAMPLE 5

Chemical Ligation with Cyanogen Bromide (CNBr)

Phosphorylated (5' or 3') oligonucleotides (100 µM) were dissolved in 250 mM MES (pH 7.6) and 20 mM $MgCl_2$ buffer. Samples were denatured by heating to 95° C., and allowed to anneal into a dumbbell complex by slowly cooling at room temperature for 1 hour, followed by cooling at 4° C. overnight. The samples were further cooled on ice (0° C.) for 15 minutes, at which time 5 M cyanogen bromide (CNBr) in acetonitrile (1/10 volume) was added. Ligation reactions utilizing CNBr were conducted in a well-ventilated fumehood. After 5 minutes, the oligonucleotides were precipitated directly from the reaction by adding 10 volumes of 2% $LiClO_4$ in acetone, cooling on dry ice for ca. 30 minutes, followed by centrifugation at 14000 rpm for 10 minutes. The pellet was washed with cold acetone (2×0.25 mL), and dried. Ligated dumbbells were analyzed and purified by denaturing polyacrylamide gel electrophoresis (PAGE; 12-20%, 8.3 M urea) and anion exchange HPLC. Prior to gel analysis and purification, the samples were heat-treated as described herein (CNIm ligation). Ligation resulted in the formation of a single new product band, which migrated faster than the corresponding nicked precursor on a denaturing polyacrylamide gel. The yield and characterization of ligated circles were determined as described herein.

EXAMPLE 6

Hybridization Studies

Thermal denaturation profiles (melting curves) were acquired on a Varian CARY 1 UV-Vis spectrophotometer (Varian, Mulgrave, Australia) equipped with a multiple cell holder, a Peltier thermal cell holder and temperature controller. Spectra were processed using CARY Win UV software (Version 2.00). The hybridization properties of oligonucleotides were investigated by monitoring the change in UV-absorbance ($\lambda$=260 nm) with increasing temperature. Hybridization buffers consisted of either: (a) 10 mM Tris-HCl, 10 mM NaCl, pH 7.5; (b) 0.25 M MES, 20 mM $MgCl_2$, pH 7.6; or (c) 10 mM $Na_2HPO_4$, 0.1 mM $Na_2EDTA$, pH 7.0. Complementary stands were dissolved in fixed ratios in 0.5-1 mL of buffer at a concentration of 4-10 µM of oligonucleotide single strands. Oligonucleotide extinction coefficients ($\epsilon_{260}$) were calculated by applying a nearest-neighbor approximation (Puglisi and Tinoco (1989) *Methods Enzymol.* 180:304-325) using an internet-based biopolymer calculator. Oligonucleotide mixtures were heated to 90° C. for 10-15 minutes in order to dissociate any non-specifically bound regions, cooled slowly to room temperature for 30 minutes and then left at 4° C. overnight. The annealed samples were transferred to pre-chilled HELLMA® QS-1.000 quartz cells (HELLMA®, Essex, UK), sealed with a TEFLON®-wrapped stopper and degassed by sonication for 15 seconds. The complexed oligonucleotides were equilibrated to 5° C. in the cell holder of the spectrophotometer for 5 minutes prior to spectral acquisition. The absorbance at 260 nm was measured at 0.5° C. intervals at a temperature rate of 0.5° C./minute.

The thermal melting temperature ($T_m$) values were calculated as the maximum of the first derivative plots of the absorbance versus temperature profiles, and coincided with the point at which half of the complexed oligonucleotides were in their single-stranded state. Spectra were typically acquired in duplicate or triplicate and the calculated $T_m$'s were consistently within 0.5-1° C. of each other. The data obtained was transferred to spreadsheet software (MICROSOFT® Excel 97) for subsequent analysis. Comparative hyperchromicity values (i.e., changes in relative absorbance) were obtained by using the formula: $H=(A_T-A_0)/A_f$, where H is the hyperchromicity, $A_T$ is the absorbance at any given temperature (T), $A_0$ is the initial absorbance reading, and $A_f$ is the absorbance at the highest temperature (Puglisi and Tinoco (1989) supra). Alternatively, normalized absorbance values (between 0 and 1) were calculated in order to compare plots of unequal hyperchromicity, such as those containing non-complementary regions (e.g., lariat DNA dumbbell) according to the equation: $A_{norm}=(A_t-A_0)/(A_f-A_0)$ (Kibler-Herzog, et al. (1993) *Anti-Cancer Drug Design* 8:65-79).

EXAMPLE 7

Preparation of HIV-RT

The p66-kDa and p51-kDA subunits of HIV reverse transcriptase were prepared by cloning into a pBAD/HisB prokaryotic expression vector (INVITROGEN™, Carlsbad, Calif.) between the XhoI and HindIII sites of the plasmid. The reverse transcriptase p66/p51 heterodimers and p51/p51 homodimers were purified in accordance with methods known in the art (Fletcher, et al. (1996) *Protein Expression and Purification* 7:27-32).

EXAMPLE 8

HIV-1 Reverse Transcriptase RNase H Inhibition

The hybrid substrate for RNase H was prepared by labeling the 5'-hydroxy termini of the RNA sequence 5'-GAU CUG AGC CUG GGA GCU-3' (SEQ ID NO:54) by the transfer of $^{32}P$ from [$\gamma$-$^{32}P$]-ATP in a reaction catalyzed by bacteriophage T4 polynucleotide kinase using standard methodologies. This labeled RNA was annealed to its complementary unlabeled DNA sequence, 5'-AGC TCC CAG GCT CAG ATC-3' (SEQ ID NO:55) to form the [$^{32}P$]-RNA/DNA hybrid substrate. Variable amounts of cold nicked and ligated RNA dumbbells were pre-incubated in 10 µL of 50 mM Tris-HCl (pH 8.0), containing 60 mM KCl, 2.5 mM $MgCl_2$ and 1.5 nM p51/p66 heterodimeric reverse transcriptase at 37° C. for 15 minutes. The reactions were initiated by the addition of [$^{32}P$]-RNA/DNA hybrid duplex substrate (50 nM final concentration), and the individual assay tubes incubated an additional 15 minutes at 37° C. An equal volume of gel loading dye (98% deionized formamide containing 10 mM EDTA, 1 mg/mL bromophenol blue and 1 mg/mL xylene cyanol) was added to the samples and the reaction products denatured by heating at 100° C. for 5 minutes. The degradation products were resolved on a 16% (19:1 crosslinking of acrylamide:bis-acrylamide) polyacrylamide sequencing gel (7 M urea) and visualized by autoradiography. The extent of cleavage of the 18-nucleotide RNA portion of the RNA/DNA hybrid was determined quantitatively by densitometric analysis (UN-SCAN-IT™ software, Silk Scientific, Orem, Utah) of the disappearance of the full-length RNA and/or the appearance of any smaller degradation products. The $IC_{50}$ values for RNA dumbbell inhibition of HIV reverse transcriptase associated RNase H activity were calculated from plots of the residual undegraded 5'-[$^{32}$P]-RNA versus dumbbell concentration.

EXAMPLE 9

RNA-Dependent DNA Polymerase Activity Assay

The unlabeled, 30-nucleotide RNA template, 5'-AUC UCU AGC AGA GGC GCC CGA ACA GGG ACA-3' (SEQ ID NO:56) (3-fold molar excess) was annealed to a 5'-[$^{32}$P]-end labeled complementary DNA primer; 5'-TGT CCC TGT TCG GGC GCC-3' (SEQ ID NO:57) in a separate reaction vessel. The RNA dumbbells (80 μM) were pre-incubated with the enzyme at room temperature for 20 minutes prior to reaction. Polymerase reactions were carried out in a 10 μL volume in the presence of 50 mM Tris-HCl (pH 8.0), 60 mM KCl, and 2.5 mM MgCl$_2$. The reaction was initiated by the addition of RNA template/5'-[$^{32}$P]-DNA primer complex and deoxynucleotide triphosphates (dNTPs, 200 nM final concentration of each) and incubated at 37° C. for 15 minutes. The polymerase activity was deactivated by the addition of an equal volume of formamide loading dye (98% deionized formamide containing 10 mM EDTA, 1 mg/mL bromophenol blue and 1 mg/mL xylene cyanol) and denatured by heating at 100° C. for 5 minutes prior to gel analysis (16%, 7M urea). The gel was visualized by autoradiography and the amount of DNA synthesized quantified by densitometric analysis using the UN-SCAN-IT™ software program.

EXAMPLE 10

DNA-Dependent DNA Polymerase Activity Assay

The ability of an RNA dumbbell to inhibit DNA synthesis from a DNA template stand was assessed using similar conditions to those used above in the RNA-dependent DNA polymerase assay. The 5'-[$^{32}$P]-DNA primer above was annealed to a 3-fold molar excess of DNA template, 5'-ATC TCT AGC AGA GGC GCC CGA ACA GGG ACA-3' (SEQ ID NO:58). All other conditions for polymerization and analysis were identical to those described above.

EXAMPLE 11

*E. coli* and Human RNase H Inhibition Assays

RNA dumbbell molecules were tested for their ability to inhibit either the *E. coli* or Human (type II) RNase H activities. RNase H mediated degradation assays were supplemented with 60 μM of cold RNA dumbbell under conditions identical to those used for HIV reverse transcriptase RNase H activity. The degradation products were quantified from the autoradiogram using the UN-SCAN-IT™ software program.

EXAMPLE 12

Crosslinking an RNase H Domain and RNA Dumbbell

Homodimeric (p51/p51) and heterodimeric (p66/p51) HIV-1 reverse transcriptase enzymes (500 ng) were incubated with ligated RNA dumbbell (50 pmol) in 50 mM Tris (pH 7.8), 50 mM KCl, and 5 mM MgCl$_2$ for 30 minutes at 37° C. The reaction mixtures were placed on ice and irradiated with a handheld UV-light (λ=254 nm) for 15 minutes. Samples were denatured by adding 2× sample loading buffer (4% SDS, 20% glycerol, 10% 2-mercaptoethanol, 125 mM Tris, pH 6.8, and bromophenol blue) and heated at 100° C. for 5 minutes. Protein complexes were partitioned on a 12% SDS-PAGE gel run at constant voltage (160 V). The gel was fixed with fixing solution (12% (w/v) trichloroacetic acid, 3.5% (w/v) 5-sulfosalicylic acid) for 30 minutes and then stained with COO-MASSIE® Brilliant Blue G-perchloric acid solution (0.04% (w/v) Brilliant Blue G in 3.5% (w/v) perchloric acid); Sigma-Aldrich, St. Louis, Mo.) for 60 minutes and rinsed with distilled water. Complexes were separated alongside molecular weight markers consisting of ovalbumin (45 KDa), bovine serum albumin (66 KDa), phosphorylase B (97 KDa) and myosin (220 KDa).

What is claimed is:

1. A composition for inhibiting the RNase H activity of a retroid virus reverse transcriptase comprising an inhibitory agent of Formula I:

Formula I wherein, $X_1$ and $X_2$ are antiparallel complementary oligonucleotide strands that associate to form a duplex;

$X_1$ is 2 to 24 nucleotides in length;

$X_2$ is 2 to 24 nucleotides in length;

$Y_1$ is 2 to 8 nucleotides in length;

$Y_2$ is 2 to 8 nucleotides in length;

at least one of $Y_1$ or $Y_2$ is 4 to 8 nucleotides in length;

$Y_1$ and $Y_2$ each independently contain a ribonucleic acid; 2',5'-linked ribonucleic acid; or combination thereof wherein a $Y_1$ or $Y_2$ of at least 4 nucleotides comprises the sequence 5'-UUYG-3'/2' (SEQ ID NO:1);

wherein the inhibitory agent comprises the nucleotide sequence set forth in SEQ ID NO:2; and wherein the inhibitory agent binds to the RNase H domain of retroid virus reverse transcriptase thereby inhibiting the RNase H activity thereof.

* * * * *

UNITED STATES PATENT AND TRADEMARK OFFICE
CERTIFICATE OF CORRECTION

PATENT NO. : 7,501,503 B2
APPLICATION NO. : 10/748475
DATED : March 10, 2009
INVENTOR(S) : Damha et al.

Page 1 of 1

It is certified that error appears in the above-identified patent and that said Letters Patent is hereby corrected as shown below:

On the Title of the patent at Item (75) Inventors:

Please delete "Rami N. Hannoush. Cambridge, MA (US):" and insert
--Rami N. Hannoush. Cambridge, MA (CA)--.

Signed and Sealed this

Ninth Day of June, 2009

JOHN DOLL
*Acting Director of the United States Patent and Trademark Office*